US008673336B2

(12) United States Patent
Parker et al.

(10) Patent No.: US 8,673,336 B2
(45) Date of Patent: Mar. 18, 2014

(54) COMPOSITION, SYSTEM, AND METHOD FOR MODULATING RELEASE KINETICS IN IMPLANTABLE DRUG DELIVERY DEVICES BY MODIFYING DRUG SOLUBILITY

(75) Inventors: Theodore L. Parker, Danville, CA (US); Stephen Hunter Diaz, Palo Alto, CA (US); John F. Shanley, Redwood City, CA (US); Diane Mai Huong Dang, Palo Alto, CA (US); Thai Minh Nguyen, Santa Clara, CA (US)

(73) Assignee: Innovational Holdings LLC, New Brunswick, NJ (US)

( * ) Notice: Subject to any disclaimer, the term of this patent is extended or adjusted under 35 U.S.C. 154(b) by 49 days.

(21) Appl. No.: 12/972,342

(22) Filed: Dec. 17, 2010

(65) Prior Publication Data
US 2011/0086082 A1 Apr. 14, 2011

Related U.S. Application Data

(63) Continuation of application No. 11/520,470, filed on Sep. 12, 2006, now abandoned.

(60) Provisional application No. 60/716,568, filed on Sep. 12, 2005.

(51) Int. Cl.
*A61F 2/00* (2006.01)
*A61K 31/497* (2006.01)

(52) U.S. Cl.
USPC .................................. 424/423; 514/252.18

(58) Field of Classification Search
USPC .................................. 424/423; 514/252.18
See application file for complete search history.

(56) References Cited

U.S. PATENT DOCUMENTS

| 4,888,354 A * | 12/1989 | Chang et al. ................ 514/424 |
| 6,378,988 B1 | 4/2002 | Taylor et al. |
| 6,395,326 B1 | 5/2002 | Castro et al. |
| 6,712,846 B1 * | 3/2004 | Kraus et al. ................ 623/1.46 |
| 2002/0122876 A1 * | 9/2002 | Modak et al. ................ 427/2.24 |
| 2004/0044405 A1 * | 3/2004 | Wolff et al. ................ 623/1.46 |
| 2004/0249449 A1 | 12/2004 | Shanley et al. |
| 2005/0107870 A1 | 5/2005 | Wang et al. |
| 2005/0143817 A1 * | 6/2005 | Hunter et al. ............. 623/11.11 |
| 2005/0169994 A1 | 8/2005 | Burke et al. |
| 2005/0186261 A1 | 8/2005 | Avelar et al. |

FOREIGN PATENT DOCUMENTS

| WO | WO 02/26162 A2 | 4/2002 |
| WO | WO2004022124 * | 3/2004 |
| WO | WO 2004/026182 A2 | 4/2004 |

OTHER PUBLICATIONS

Li et al, Investigation of Solubility and Dissolution of a Free-Base and Two Different Salt Forms as a Function of pH, Pharmaceutical Research, vol. 22, No. 4, Apr. 2005, pp. 628-635.*
Berge, et al., "Pharmaceutical Salts", Journal of Pharmaceutical Sciences, vol. 66, No. 1, Jan. 1977, pp. 1-19.
Duchene, et al., "Pharmaceutical Uses of Cyclodextrins and Derivatives", Drug Development and Industrial Pharmacy, vol. 16, No. 17, 1990, Abstract.

* cited by examiner

*Primary Examiner* — Brian-Yong Kwon
*Assistant Examiner* — Jennifer A Berrios

(57) ABSTRACT

An implantable drug delivery device loaded with a beneficial agent is provided, wherein the beneficial agent is in two different forms, a first form having a higher solubility and a second form having a lower solubility, and wherein the two different forms are present in a proportion which is selected to achieve a desired release rate.

20 Claims, 5 Drawing Sheets

COMPOSITION, SYSTEM, AND METHOD FOR MODULATING RELEASE KINETICS IN IMPLANTABLE DRUG DELIVERY DEVICES BY MODIFYING DRUG SOLUBILITY

RELATED APPLICATIONS

This application is a Continuation of Ser. No. 11/520,470 filed on Sep. 12, 2006, which claims priority under 35 U.S.C. §119(e) to U.S. provisional patent application No. 60/716,568, filed Sep. 12, 2005. The complete disclosures of the aforementioned related U.S. patent applications are hereby incorporated herein by reference for all purposes.

BACKGROUND OF THE INVENTION

1. Field of the Invention

The present invention relates to devices, systems, and processes useful as implantable delivery device, and more specifically to an implantable delivery device which can deliver a drug to a body in two forms having different solubilities for the purpose selecting a desirable release rate.

2. Brief Description of the Related Art

In the area of local drug delivery, such as in drug eluting stents and other implantable drug delivery devices, the control of release kinetics is important to achieving the desired clinical results. For example, it is often desirable to deliver a drug locally over time periods of days, weeks, or longer. It has been found that highly water soluble drugs when coated onto a stent or other implantable device with or without a polymer will be released very fast due to the high water solubility of the drug. Less water soluble drugs are released at a slower rate from similar systems. Often this slower rate is more desirable for local sustained release applications.

The slow or sustained release used in local delivery is generally just the opposite of the desirable release for systemic delivery of a drug by an oral tablet or capsule which requires high water solubility and quick release in a matter of minutes or hours. Accordingly, when a drug intended for oral or other systemic delivery is adapted for local delivery in an implantable medical device, it may be desirable to alter the drug form to achieve a lower solubility and a slower and more sustained release for delivery over many hours and preferably days.

In local drug delivery, either solely the salt (ionic) form of the drug or solely the purely neutral form are delivered. The rate of drug delivery is controlled by the choice of excipient or matrix, but not by the form of the drug. One example of this is in drug eluting stents where the polymer matrices containing the drug are chosen to achieve the desired release kinetic. This often means that non-biodegradable hydrophobic polymers are used to control and slow down the release of the drug.

SUMMARY OF THE INVENTION

According to a first aspect of the invention, an implantable drug delivery device is provided comprising an implantable device configured to be implanted within tissue, lumens, organs of the body; a beneficial agent provided in or on the implantable medical device for delivery to the tissue, lumen, or organ of the body to achieve a desired beneficial effect; wherein the beneficial agent is provided in two different forms, a first form having a higher solubility and a second form having a lower solubility, and wherein the two different forms are present in a proportion which is selected to achieve a desired release rate.

According to another aspect of the present invention, a method of forming an implantable drug delivery device is provided comprising selecting an implantable device configured to be implanted within tissue, lumens, or organs of the body; providing a beneficial agent in two different forms, a first form having a higher solubility and a second form having a lower solubility; selecting a proportion of the two different forms to achieve a desired release rate; and affixing the beneficial agent in the two different forms of the beneficial agent and in the selected proportion to the implantable device.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which.

DETAILED DESCRIPTION OF EXEMPLARY EMBODIMENTS

Figure 1:
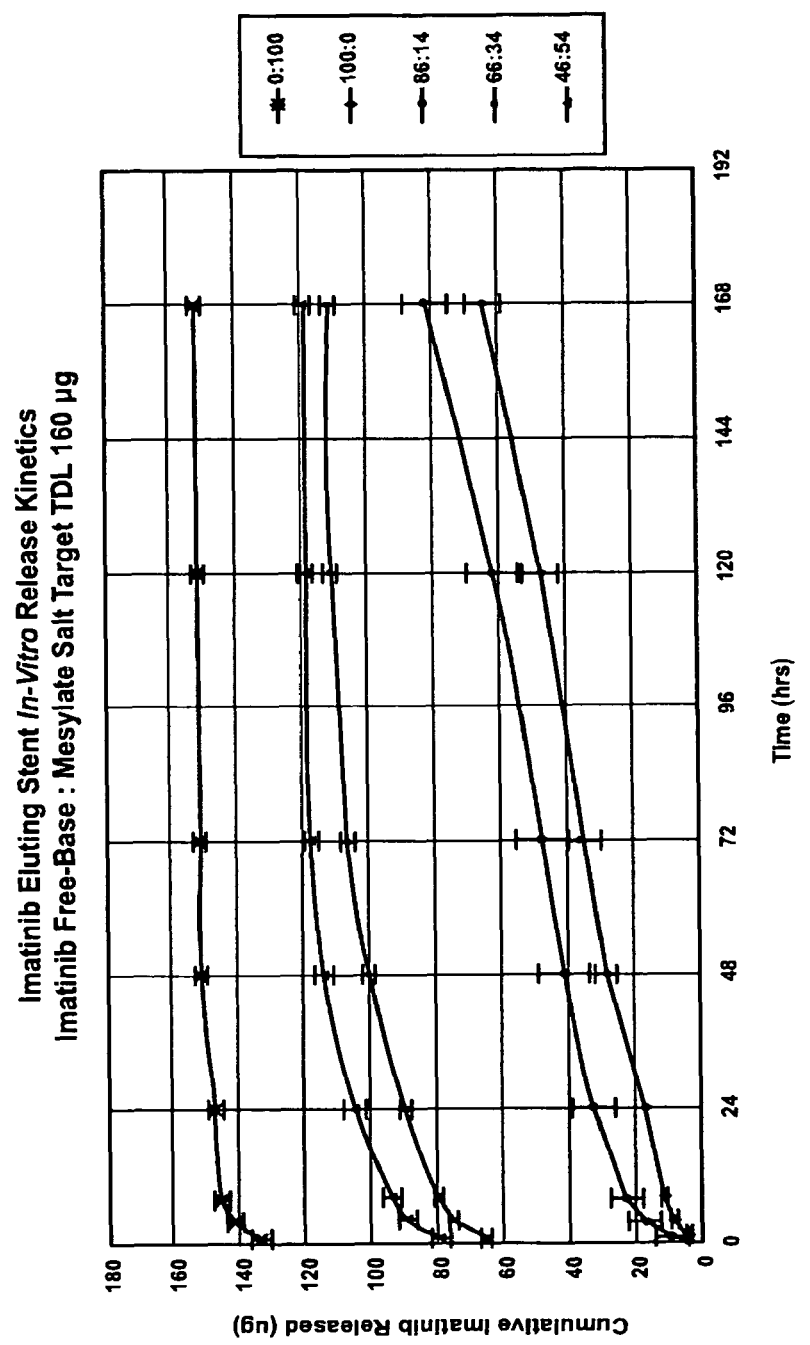
FIG. 1 is a graph of the cumulative release from low dose imatinib stents having different proportions of imatinib mesylate salt and imatinib free-base. The total drug load was 160 μg.

The terms "agent" or "beneficial agent" as used herein are intended to have the broadest possible interpretation and are used to include any therapeutic agent or drug, as well as inactive agents such as barrier layers, carrier layers, therapeutic layers, or protective layers.

The terms "drug" and "therapeutic agent" are used interchangeably to refer to any therapeutically active substance that is delivered to a bodily lumen of a living being to produce a desired, usually beneficial, effect. Beneficial agents may include one or more drug or therapeutic agent.

The terms "openings" and "holes" includes both through openings and recesses.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a Mw greater than about 3000 and preferably greater than about 10,000 and a Mw that is less than about 10 million, preferably less than about a million and more preferably less than about 200,000. Examples of polymers include but are not limited to, poly-α-hydroxy acid esters such as, polylactic acid (PLLA or DLPLA), polyglycolic acid, polylactic-co-glycolic acid (PLGA), polylactic acid-co-caprolactone; poly(ester-co-amide) copolymers; poly(block-ethylene oxide-block-lactide-co-glycolide) polymers (PEO-block-PLGA and PEO-block-PLGA-block-PEO); polyethylene glycol and polyethylene oxide, poly(block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

The term "primarily" with respect to directional delivery, refers to an amount greater than about 50% of the total amount of therapeutic agent provided to a blood vessel is provided in the primary direction.

Water soluble forms of a drug will elute faster than less water soluble forms of the same drug. The invention involves modulating the rate of local in vivo delivery of a drug substance that is capable of existing in a first less water soluble form and a second more water soluble form. The release rate is modulated by controlling the relative proportion of a more slowly eluting form to a more rapidly eluting form in the overall dose to be delivered. Control of the water solubility of the agent to be delivered can be achieved in a number of ways, some of which will be described herein. The multiple forms of the same drug which can be created each with different solubilities are used together.

When a specific release kinetic is desired for local delivery, two or more forms of the drug with different solubilities can be combined in a proportion which is selected to achieve the desired release kinetic profile.

Modifying the Ionic/Neutral Form

A first method to modulate the rate of drug release, or elution, from a device is to control the proportion of a more water soluble ionic or salt form of a drug to a less water soluble neutral form of the drug contained on or within the device, such as a stent.

To be effectively delivered orally, many drugs must be converted from a neutral, non-ionic form (for example, a free base form) to a more water soluble ionic form (for example, a salt). For drugs containing what are generally called basic functional groups, this can be accomplished by creating the ionic salt form by addition of an acid sufficiently strong to protonate the basic moiety. For drugs that contain what are generally called acidic functional groups, this can be accomplished by creating the ionic salt form by addition of a base sufficiently strong to de-protonate the acidic functionality to produce the so-called conjugate base form. Although this approach is optimal for oral delivery, in the case of local delivery, the rate of elution of the purely ionic form of the drug can be more rapid than desired for a sustained delivery system.

The ionic form of a molecule (including a drug molecule) will be more water soluble than the non-ionic form; the in vivo elution rate is related to the water solubility. Consequently, by the method of this invention, the rate of elution of the drug from the local delivery device may be modulated by specifying the relative proportion of ionic and non-ionic forms of the drug in the total drug loaded on the local delivery device.

Generally, the rate of delivery of the ionic, salt form of many drugs is too rapid to provide a desirable "sustained delivery" system. It is envisioned that by converting a portion or all of a drug into its free base form, the rate of delivery will be decreased and the duration of delivery will be increased. By specifying the relative proportions of salt and free base forms, the rate and duration of drug delivery may be effectively controlled to a desired range to optimize its physiologic effect.

Drugs which are available in an ionic form and can be converted to a free base or neutral form include, but are not limited to:

| Drug | Free Base-Salt forming group |
|---|---|
| Gleevec | pyrimidinyl, piperizinyl |
| Midostaurin | amino |
| Cladribine | purinyl |
| Clotrimazole | imidoxolyl |
| Farglitazar | oxazolyl |
| Epothilone D | thiazolyl |
| Mitoxanthrone | amino |
| Rosigitazone | amino, pyrindinyl |
| Pioglitazone | amino, pyrindinyl |
| Probucol | phenolic |
| Dipyridimole | amino, piperidnyl |

Other drugs which can be converted to the salt form include those containing the following radicals:

2H-Pyrrolyl, Pyrrolyl, Imidazolyl, Pyrazolyl, Pyridyl, Pyrazinyl, Pyrimidinyl, Pyridazinyl, Indolizinyl, Isoindolyl, Indolyl, Indazolyl, Purinyl[1], 4H-Quinolizinyl, Isoquinolyl, Quinolyl, Phthalazinyl, Naphthyridinyl, Quinoxalinyl, Quinazolinyl, Cinnolinyl, Pteridinyl, 4aH-Carbazolyl[1], Carbazolyl[1], β-Carbolinyl, Phenanthridinyl, Acridinyl[1], Perimidinyl, Phenantrholinyl, Phenazinyl, Isothiazolyl, Thiazolyl, Pyrrolidinyl, Pyrrolinyl, Phenothiazinyl, Phenoxazinyl, Imidazolidinyl, Imidazolinyl, Pyrazolidinyl, Piperidyl[3], Piperazinyl, Indolinyl, Isoindolinyl, Quinuclidinyl, Morpholinyl[1], Purinyl, and Guanidino.

Drugs that are able to exist in either a neutral or conjugate base form include those containing the following acid groups: carboxylic acid, sulfonic acid, phosphoric acid, sulfonic acid, and phenolic hydroxyl.

In addition to the general concept of using the salt form and neutral form of a drug, an even greater control of drug elution rate can be obtained by selection of relatively more or less hydrophobic or hydrophilic counter-ions for the ionic or salt form of the drug.

For example, if the drug contains a conjugate base functionality, alkali metal counter cations (e.g., Li+, Na+, K+) would confer greater water solubility and faster elution rate than quaternary ammonium counter cations (e.g., benzyltrimethylammonium, also known as benzalkonium). If the drug contains a base functionality in the neutral form, protonation by an acid giving a halogen counter anion (e.g., chloride, bromide), would render the ionic form more water soluble and more rapidly eluting that if the counter anion were a carboxylate anion, particularly a fatty acid carboxylate (e.g., laurate, palmitate, stearate).

Further, it is envisioned that control of the elution rate of the purely ionic form of the drug (no neutral form present) may be obtained by the relative proportions of the ionic drug with a relatively hydrophilic counter-ion and a relatively hydrophobic, though still water soluble, counter-ion (ether counter-cation or counter-anion depending on the neutral structure of the drug, i.e., whether the neutral drug is an acid or a base).

Additionally, the neutral form of a drug is more hydrophobic than the ionic form, so the neutral form will generally have a greater solubility in the matrix material, such as an organic polymer material, which can be used to slow the elution rate. Experience has shown that as the total drug loading of a water soluble drug is increased, the proportion of drug released initially in a so-called burst release is greatly increased. It is known that a drug that is soluble in the delivery matrix will elute more slowly than a drug that is in a separate phase, so a higher loading of drug that can be controlled to be more slowly eluting can be achieved by increasing the proportion of the neutral, non-ionic drug form.

Implantable Drug Delivery Forms

In the examples herein, the drug may be delivered from reservoirs or holes in an implantable stent. When delivered from a stent, the agent may be provided in any known polymer, and preferably a biodegradable or bioresorbable polymer. To provide primarily luminal delivery of an agent, the agent deposit is covered with a polymer deposit which acts as a cap and substantially prevents mural delivery. The polymer cap can be formed of a slower degrading polymer than the polymer used with the agent. Alternatively, to provide primarily mural delivery, the agent deposit can be placed on a polymer deposit which acts as a base and substantially prevents luminal delivery.

Many alternatives exist for local delivery of drugs from implantable medical devices. The stents with holes forming drug delivery reservoirs described above are one example. Other examples include microspheres, microparticles, nanospheres, nanoparticles, implantable osmotic devices, stents or other implants incorporating drug by coating, affixing threads, microspheres, or sleeves. The implantable device can be metallic, polymer, or other biocompatible material and can be bio-erodible, permanent, or partially bio-erodible. Each of these implantable local drug delivery devices can benefit from the combination of different forms of the same drug to decrease drug solubility, slow release rate, and extended release by using the free-base, soft counter ion, or one of the other methods which will be discussed below.

Using An Inclusion Complex

A second method of controlling the water solubility of a more hydrophobic drug is by creating a non-covalent complex of the drug with a more hydrophilic complexation agent. An inclusion complex is a way of making a neutral, hydrophobic drug more water soluble. Such complexes are well known as a method of increasing the water solubility of hydrophobic drugs, particularly for oral delivery. By selecting the amount of complexation agent such that there is less agent than necessary to achieve total solubility of all the drug, the ratio of a more water soluble form to a less water soluble form can be controlled and hence the rate of release or elution of drug from a device can be modulated. Such complexes often occur in integer molar ratios, such as 1:1 or 2:1, so that by selection of the amount of complexation agent, the relative proportion of more water soluble to less water soluble drug forms can be controlled.

Complexes of agent and drug can be inclusion complexes, such as formed by cyclodextrin and sulfobutyl cyclodextrin which have a hydrophilic exterior and a hydrophobic interior that can accommodate a hydrophobic drug to increase its water solubility. Thus, by specifying the relative molar proportions of drug and cyclodextrin, the relative amounts of fast eluting complexed drug and slow eluting un-complexed drug can be controlled, which will allow control of the overall release kinetics. Additionally, if a portion of a drug substance can be held in a clathrate structure, that portion of the overall drug dose will be released more slowly, thus allowing modulation of the release.

Using Solubilization Agents

A third method of controlling the water solubility of a generally hydrophobic drug is by the addition of stabilizers, meaning compounds that stabilize the amount or concentration of a drug substance in an aqueous based or physiologic solution. Stabilizers can be surfactants, emulsifiers, hydrotropes, etc. Such molecules are often amphiphilic, where one section of the molecule is relatively more hydrophilic and another section is relatively more hydrophobic. It has been found that the maximum solubility of hydrophobic drugs is proportional to the amount of stabilizer present. Consequently, it is envisioned to modulate the release rate of a hydrophilic drug by specifying the level of stabilizer at or below the level required for complete solubility. Thus, a portion of the drug dose will be more soluble due to the interaction with the stabilization agent, which the remaining portion will be less soluble based on the structure of the drug. Again, the overall drug release rate will be modulated by the level of stabilizer incorporated into the overall drug formulation. Example agents envisioned are amphiphilic, ionic and non-ionic agents such as the polysorbates, Tween, and Brij materials, PEO-glycerol-fatty acid esters, and phospho-lipids such as phosphoryl choline, DPPC, DPPE, DPP inositol and PEO-PC adducts.

Changing Crystalline Form

A fourth method of controlling the water solubility of a drug is controlling the relative proportions of different crystalline forms of the drug. For example, some drugs occur in both a less rapidly dissolving crystalline lattice form and a more rapidly dissolving amorphous form.

This would be most practically accomplished by segregating the crystalline form into one reservoir or area on the delivery device, and the amorphous form to another. Although thermodynamically the eventual solubility of the drug forms is identical, kinetically the drug in the amorphous form will be solubilized more rapidly than that in the crystalline form, thus allowing modulation of the overall drug release profile.

Some drugs have crystalline forms that contain water of crystallization and are often more rapidly solubilized into aqueous systems than the same drug occurring in a second crystalline form not including water of crystallization.

A polymorph is just one of the various crystalline lattice forms ("morphologies") that a drug can exist in. In addition to the "pure drug" crystalline forms, of which there may be several, many drugs can form crystalline forms that include a specific number of solvent molecules in the lattice (such as the water of crystallization in a hydrate form). So, solvates are just like hydrates, except an organic solvent takes the place of water. Different solvate crystalline forms of a drug will have both different solubility and different Intrinsic Dissolution Rates (IDR's), which will translate into different elution rates. Thus, solubility can be different for the same drug in different crystalline forms, with different anhydrate, or with different solvates.

In the method of the invention, the overall delivery profile can be tailored by combining the effects of the excipient/matrix and the effects of the form of the drug, since the form of the drug affects the water solubility, lipid solubility, hydrophilic-hydrophobic balance, etc., central to controlling the mobility of the drug. The hydrophilic-hydrophobic balance of the free base structure, neutral structure, or conjugate base structure is useful in developing the proportions of neutral (non-ionic) and ionic forms of the drug to achieve a particular desired elution profile. Hydrophobicity may be determined experimentally by the oil-water portioning constant (Pow) (larger values are more hydrophobic) or by calculation of the Hansen solubility parameter (lower values are more hydrophobic).

EXAMPLES

The following non-limiting Examples are provided to further illustrate the preferred embodiments of the present invention.

Example 1

In the case of imatinib, the ionic form (Gleevec or imatinib mesylate) is made by reaction with an acid. Conversely, if the neutral form is inherently an acid, the reaction with a base will give the acid form. For imatinib mesylate, which is already in the salt form, the drug is reacted (de-protonated) with a base stronger than imatinib itself, such as sodium carbonate. The acid will then neutralize—makes the salt of—the strongest base present.

The following method was followed for preparation of imatinib free base from imatinib mesylate salt.

1) A solution was prepared by combining imatinib mesylate salt, MW 589.7 g/mole, 5.9 g and water, 100 mL, to make a 0.1 Molar solution.

2) A second solution was prepared by combining sodium carbonate, MW 106 g/mole, 10.6 g and water, 100 mL, to make a 1.0 Molar solution.

3) A 20 ml vial with screw cap was fitted with a magnetic stirrer and placed on a stirring plate.

4) A 4 mL aliquot of the imatinib mesylate salt, solution, 0.4 mmoles salt, was added to the beaker and stirring begun.

5) A 0.5 mL aliquot of the sodium carbonate solution, 0.5 mmoles $Na_2CO_3$ (25% molar excess), was added drop-wise to the stirred solution. imatinib free base precipitated from the solution.

6) The vial was sealed with a screw cap and held in a refrigerator at 2-4 C for 16 hours.

7) The vial was removed, then centrifuged for two minutes, and the clear supernatant decanted from the precipitated white free base.

8) The free base was washed with 10 mL aliquots of ice water, centrifuged, and the supernatant decanted. The pH of the supernatant was measured with a pH strip.

9) The washing process was repeated until the supernatant was neutral (pH 7).

10) After the last washing step, the precipitated free base was dried under vacuum (>29 in. Hg) at ambient temperature overnight to provide imatinib free base as a white powder.

The imatinib free-base (slow release) and the imatinib meslate salt (Gleevec) were loaded into holes in stents in a polymer matrix of PLGA 85/15 with a PLGA 85/15 base and cap and the release from the stents was recorded in FIG. 1. A solvent such as NMP or anisol was used to deposit the drug/polymer compositions and then evaporated. The releases shown in FIG. 1 are the average of three stents each. Methods and systems for depositing polymers and drugs within holes in stents are described further in WO 2004/026182 which is incorporated herein by reference.

As shown in FIG. 1, the free base gives the slowest release and the salt provides the fastest release. The dosage for this example was about 160 micrograms normalized for a 16 mm long stent. The free base and salt forms where then combined in the ratios of 86:14, 66:34, and 46:54 and it was shown that the rate of the release (solubility of the drug) is proportional to the percentage of free base or salt. Thus, the selection of a percentage of free base and salt can be used to provide a selected drug release kinetic.

As can be seen in FIG. 1, the release of the salt form alone is essentially complete in about 48 hours. The addition of the free-base form allows the release to be extended past 48 hours to about 72 hours for a formulation of 46% free base and to about 120 hours for a formulation of about 66% free base. While a formulation with 86% free base continues to release imatinib in-vitro at 168 hours and beyond.

Example 2

Figure 2:
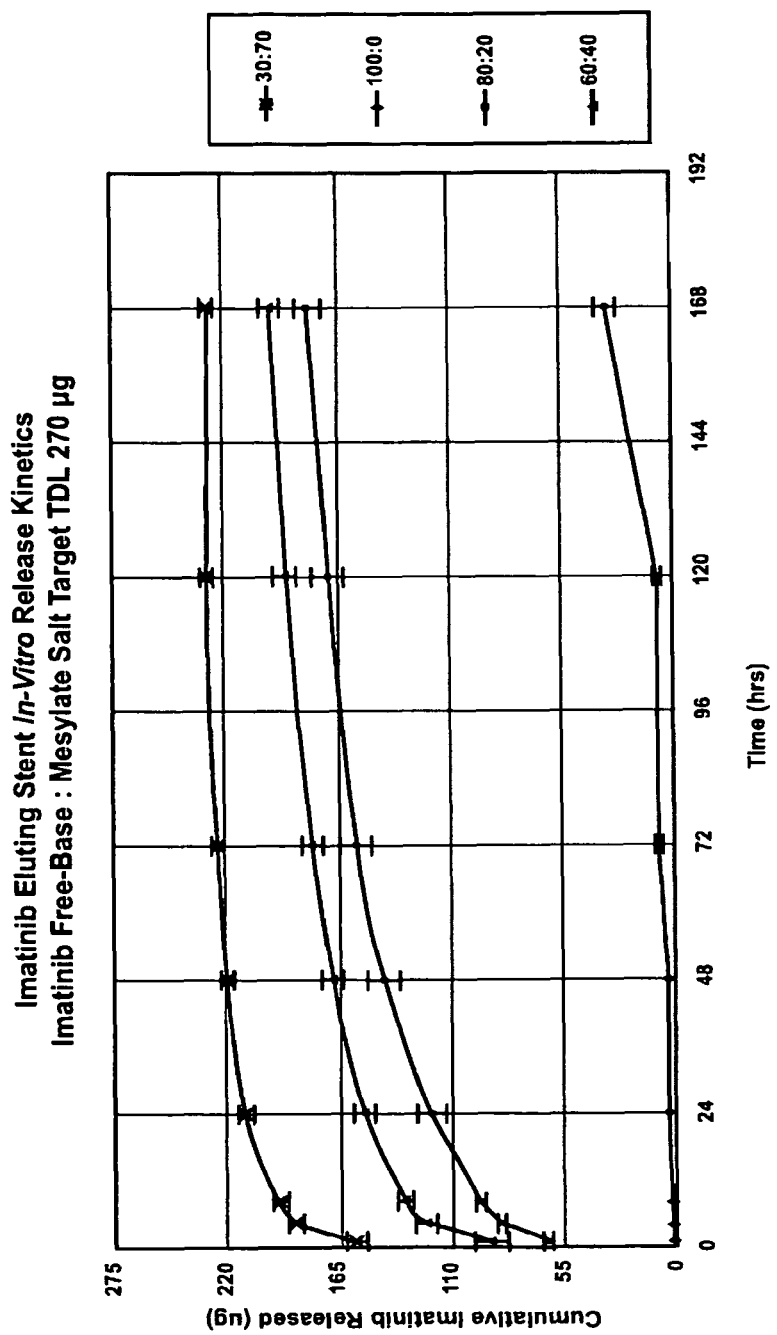
FIG. 2 is a graph of the cumulative release from high dose imatinib stents having different proportions of imatinib mesylate salt and imatinib free-base. The total drug load was 270 μg.

The same procedure was repeated for a higher dose of about 270 micrograms and the release is shown in FIG. 2. In this example, PLA-PCL was added to the PLGA base to form a 50/50 mixture while the matrix for the drug and the cap were PLGA as in Example 1. This example shows a similar result that the release rate can be slowed by addition of the free-base form of the drug and the selection of a desired release kinetic can be achieved by selecting the proportion of free-base to salt.

Example 3

Figure 3:
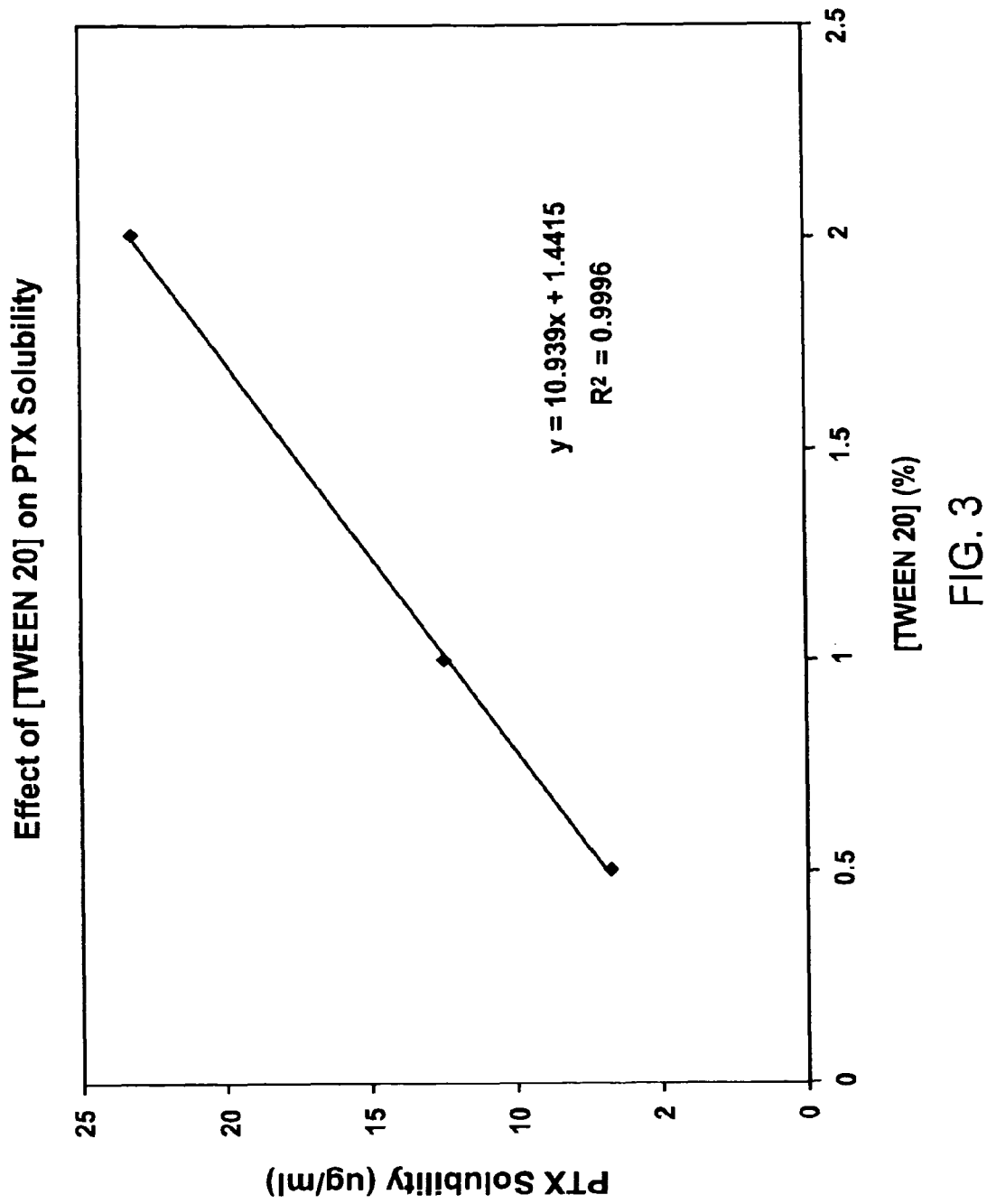
FIG. 3 is a graph of the solubility of paclitaxel formulated with different amounts of the solubilization agent Tween.

FIG. 3 illustrates the linearity of the effect of TWEEN 20 on solubility of paclitaxel. The solubility of the paclitaxel is proportional to the amount of TWEEN 20 included in the formulation. More specifically, the solubility of paclitaxel increased proportionally to the concentration of TWEEN 20. Thus, for faster releasing paclitaxel formulations a solubilizing agent, such as TWEEN can be used.

Example 4

Figure 4:
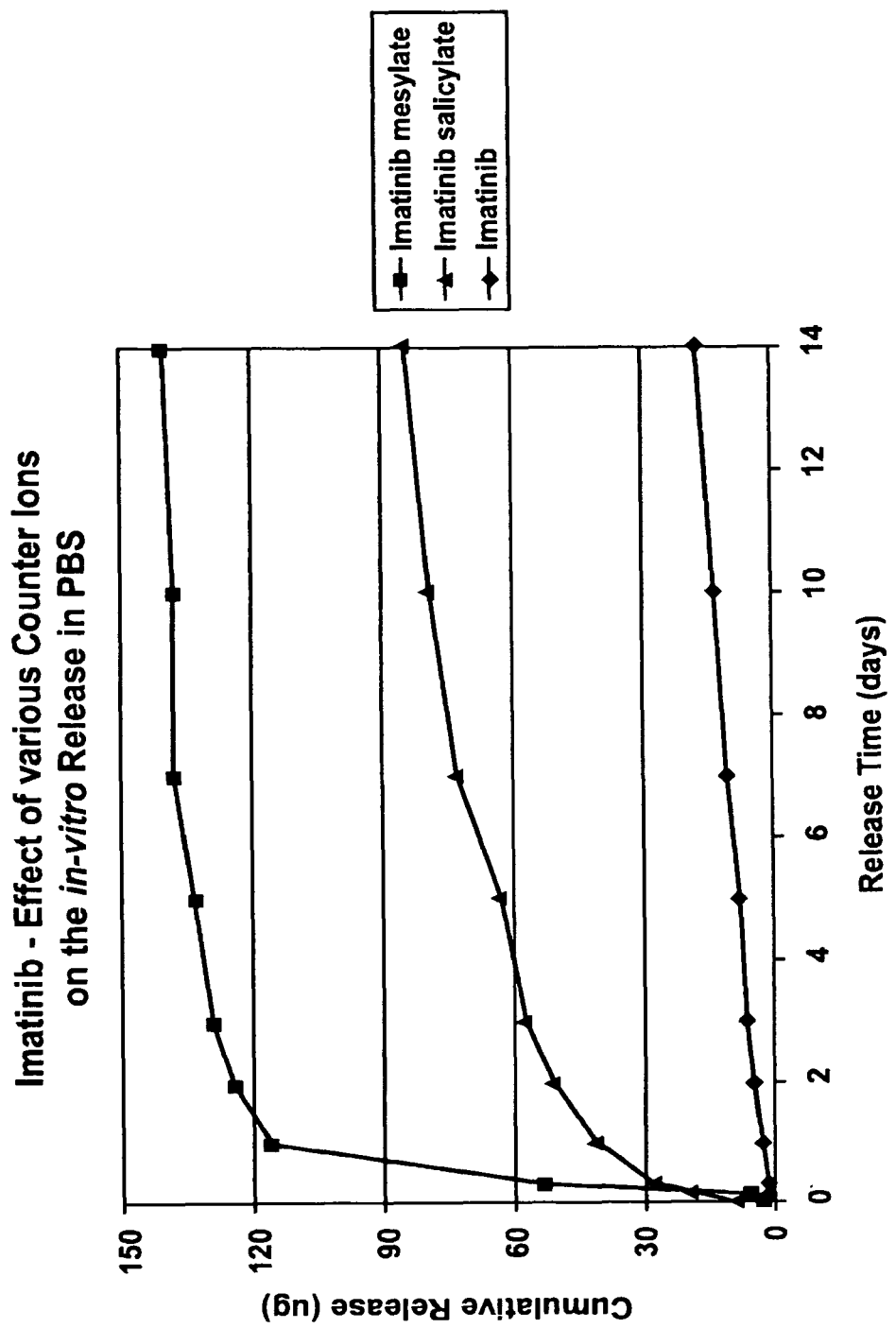
FIG. 4 is a graph of the effect of various counter ions on the in vitro release of the salt form of imatinib.

FIG. 4 illustrates the effect of several counter ions on the in vitro release of a drug, in this example imatinib. Total drug load was 150 μg to 200 μg. PLA-PLC was used in the base and cap while the matrix containing the drug was PLGA as in Examples 1 and 2. As plainly illustrated in the figure, imatinib mesylate achieved a significantly higher cumulative release, relatively quickly, than imatinib salicylate, which itself was significantly higher that that of imatinib.

Example 5

Figure 5:
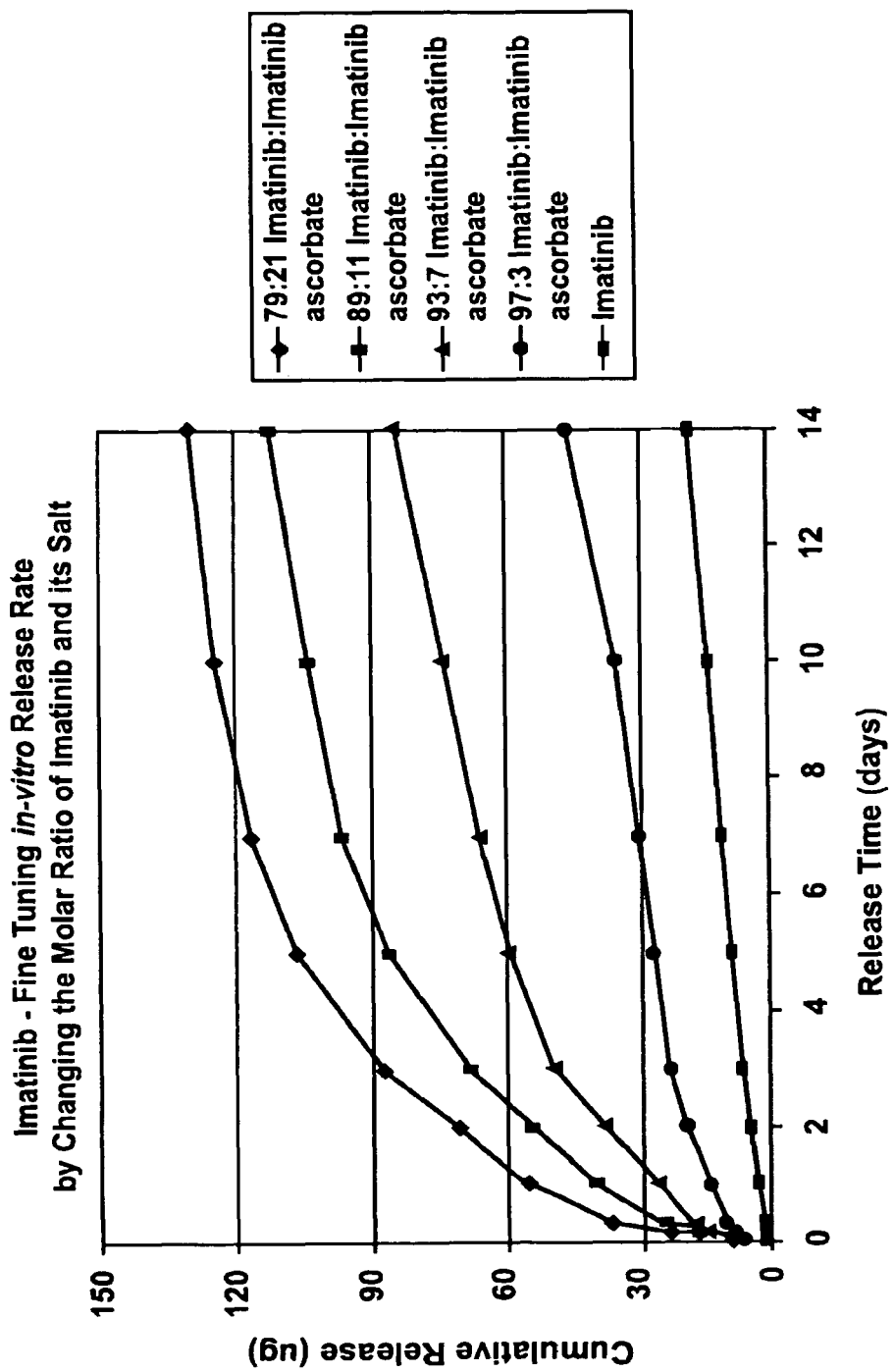
FIG. 5 is a graph of the release rates from imatinib stents having different molar ratios of imatinib and its salt.

FIG. 5 illustrates the effect of changing the molar ratio of a drug, in this example imatinib, to its salt on the in vitro release of the drug. Again, PLA-PCL was used in the base and cap while the matrix containing the drug was PLGA. The total drug load was 150 μg. As plainly illustrated in the figure, lower ratios of imatinib to the salt imatinib ascorbate resulted in significantly higher release rates.

While the invention has been described in detail with reference to exemplary embodiments thereof, it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. An implantable drug delivery device comprising: an implantable device configured to be implanted within tissue, lumens, or organs of the body; a beneficial agent provided in or on the implantable medical device for delivery to the tissue, lumen, or organ of the body to achieve a desired beneficial effect; wherein the beneficial agent is provided in two different forms, a first form having a higher solubility and a second form having a lower solubility, and wherein the two different forms are present in a proportion which is selected to achieve a desired release rate that is different from both a release rate of the first form alone and a release rate of the second form alone; wherein the beneficial agent is imatinib and the first form is a free-base form of imatinib and the second form is a salt form of imatinib.

2. The device of claim 1, wherein the implantable device is microspheres, microparticles, nanospheres, or nanoparticles.

3. The device of claim 1, wherein the implantable device is a metallic implant.

4. The device of claim 1, wherein the implantable device is a stent.

5. The device of claim 1, wherein beneficial agent is coated on the implantable device.

6. The device of claim 1, wherein the beneficial agent contained in reservoirs in the implantable medical device.

7. The device of claim 6, wherein the different forms of the beneficial agent are contained in different reservoirs.

8. The device of claim 6, wherein the different forms of the beneficial agent are contained in the same reservoir.

9. The device of claim 1, wherein the first form includes an inclusion complex and the second form includes no inclusion complex or less inclusion complex than the first form.

10. The device of claim 1, wherein the first form includes a solubilization agent and the second form includes no solubilization agent or less solubilization agent.

11. A method of forming an implantable drug delivery device comprising: selecting an implantable device configured to be implanted within tissue, lumens, or organs of the body; providing a beneficial agent in two different forms, a first form having a higher solubility and a second form having a lower solubility; selecting a proportion of the two different forms to achieve a desired release rate; affixing the beneficial agent in the two different forms and in the selected proportion to the implantable device; wherein the beneficial agent is imatinib and the first form is a free-base form of imatinib and the second form is a salt form of imatinib.

12. The method of claim 11, wherein the two different forms of the beneficial agent are mixed together before affixing to the implantable device.

13. The method of claim 11, wherein the two different forms of the beneficial agent are maintained separate when affixed to the implantable device.

14. The method of claim 11, wherein the implantable device is microspheres, microparticles, nanospheres, or nanoparticles.

15. The method of claim 11, wherein the implantable device is a metallic implant.

16. The method of claim 11, wherein the implantable device is a stent.

17. The method of claim 11, wherein beneficial agent is coated on the implantable device.

18. The method of claim 11, wherein the beneficial agent is contained in reservoirs in the implantable medical device.

19. The method of claim 11, wherein the first form includes an inclusion complex and the second form includes no inclusion complex or less inclusion complex than the first form.

20. The method of claim 11, wherein the first form includes a solubilization agent and the second form includes no solubilization agent or less solubilization agent.

* * * * *